United States Patent [19]

Lesley et al.

[11] Patent Number: 4,854,726
[45] Date of Patent: Aug. 8, 1989

[54] THERMAL STRESS SCREENING SYSTEM

[75] Inventors: Arthur M. Lesley, Woodland Hills; William Jaron, Camarillo, both of Calif.

[73] Assignee: Hughes Aircraft Company, El Segundo, Calif.

[21] Appl. No.: 868,413

[22] Filed: May 29, 1986

[51] Int. Cl.⁴ .......................................... G01N 25/00
[52] U.S. Cl. ...................................... 374/45; 374/57; 73/865.6; 165/61; 165/27; 62/298
[58] Field of Search ............... 374/45, 50, 57, 4, 5; 73/865.6; 165/61, 63–66, 27; 62/298, 299, 125–127; 219/279, 280, 366, 369, 371, 374–377, 351; 126/99 R, 107, 108, 110 R, 226, 229, 231; 237/50

[56] References Cited

U.S. PATENT DOCUMENTS

| | | | |
|---|---|---|---|
| 2,022,133 | 11/1935 | Morse et al. | 165/61 |
| 2,082,230 | 6/1937 | Stout et al. | 165/65 |
| 2,597,026 | 5/1952 | Patton | 126/99 R |
| 2,776,118 | 1/1957 | Davis | 165/61 |
| 2,894,728 | 7/1959 | Davis | 165/61 |
| 3,252,508 | 5/1966 | Goettl | 165/63 |
| 3,665,727 | 5/1972 | Mather | 62/298 |
| 3,712,078 | 1/1973 | Maynard et al. | 62/298 |
| 4,008,756 | 2/1977 | Hufford | 165/27 |
| 4,033,140 | 7/1977 | Klee et al. | 62/298 |
| 4,311,439 | 1/1982 | Stofen | 62/298 |
| 4,337,823 | 7/1982 | DelPercio | 219/366 |
| 4,572,283 | 2/1986 | Vanderschaaf | 165/61 |
| 4,575,257 | 3/1986 | Ogura et al. | 374/57 |

FOREIGN PATENT DOCUMENTS

| | | |
|---|---|---|
| 1485027 | 5/1967 | France . |
| 2063958 | 7/1971 | France . |
| 2172535 | 9/1973 | France . |
| 125551 | 7/1985 | Japan . |

Primary Examiner—William A. Cuchlinski, Jr.
Assistant Examiner—Patrick R. Scanlon
Attorney, Agent, or Firm—J. E. Holman

[57] ABSTRACT

An environmental chamber for providing thermal stress screening is comprised of a plurality of modular components which may be quickly assembled and disassembled for ease of maintenance and repair. In particular, a heater/cooling unit is coupled by means of a plurality of quick release lockable fasteners to a plenum miodule. The plenum module in turn is coupled by means of additional quick release lockable fasteners to a blower module. The plenum module in turn is comprised of a heater plenum which communicates with a blower plenum. Gas drawn into the heater plenum and passed over heating coils which are disposed into the heating plenum from the heating/cooling module. The gas is then communicated to a blower plenum. Cryogenic nitrogen gas is constantly bled through a small (0.015") hole of the liquid nitrogen valve body and is selectively provided to the blower plenum from the heating/cooling module. The selectively heated or cooled gas is then expelled from the blower plenum by means of a blower which extends into the blower plenum from the blower module. Selective heated and cooled gas is directed to a part under test as selectively activated through proportional, integral and derivative control in response to the temperature requirements of the part under test and not in response to the gas delivered to the part or from the blower plenum.

5 Claims, 10 Drawing Sheets

THERMAL STRESS SCREENING SYSTEM

BACKGROUND OF THE INVENTION

1. Field of the Invention

The invention relates to the field of environmental chambers and in particular to an apparatus and method for thermal stress screening of electronic circuitry and assemblies.

2. Description of the Prior Art

The design of environmental chambers has previously not been subject to radical changes from year to year due to the reasonably well fixed or established purposes for which such chambers are used. However, currently significant modifications have been made in these purposes. For example, the environmental changes to which circuits and to which circuit assemblies are subjected in increasingly complex applications in aerospace, near space or outer space, have placed new demands upon reliability as well as environmental cycling which such circuits must withstand. Environmental chambers must create similar environmental stresses on the earth's surface as these circuits will encounter in their ultimate applications In particular there is a growing demand for environmental chambers capable of producing faster thermal changes, for customized designs for unique configurations of chambers for stress screening, and for microprocessor based programmable control of such chambers In addition, there is a recognized need for ease of maintenance and repair of the environmental chambers Many electronic hardware markets are moving toward 100% testing in some form of temperature cycling of their PC boards, assemblies and final products Failure of the environmental control testing equipment thus becomes a critical manufacturing blockage. Downtime of the environmental test equipment is then translated directly into lost production output.

Furthermore, the accuracy or reliability of the environmental testing itself must be insured if the test certification is to have any validity. In other words, if a circuit assembly is certified as operable in a temperature range even under specified thermal stresses, the test procedure must reliably and actually cycle the circuit assembly across the specified range and at the specified rate. Prior art environmental chambers were controlled so that the chamber environment was cycled through the specified ranges and rates, but it could not be certified that the tested object or circuit assembly actually achieved the specifications. A survey of test procedures and of specific environmental apparatus is set forth generally in a review article entitled "Environmental Screening/-Chambers-Faster Cycling, Smarter Controls Typify New Chamber Designs", Evaluation Engineering, May 1985.

What is needed, then, is an apparatus and method which overcomes each of these defects of the prior art. More specifically, what is needed is a temperature control system which can be easily and quickly customized for unique configurations, quickly and easily repaired with minimal downtime, programmably controlled, and which reliably and accurately cycles the tested object through specification ranges and rates.

BRIEF SUMMARY OF THE INVENTION

The invention is a modular apparatus for providing thermal stress screening of a part under test comprising a first unit for providing heating and cooling, a second unit for blowing gas, a third unit including an intake and output plenum, and a quick release mechanism for coupling the first and second unit to the third unit in an operative configuration. The quick release mechanism permits coupling and decoupling of the first and second unit to and from the third unit without expenditure of substantial time and effort. As a result the apparatus may be reconfigured and quickly accessed for repair and maintenance.

The quick release mechanism comprises a plurality of quick release lockable fasteners having two opposing ends. One end of the fastener is coupled to the third unit and the opposing end of each fastener is selectively coupled to the first and the second unit.

The third unit comprises a separate intake and output plenum. The intake and output plenums communicate with each other. The first unit for providing heating/cooling is disposed in the intake plenum. The second unit for blowing gas is disposed in the output plenum.

The first unit for providing heating/cooling comprises heater unit and cryogenic gas injection unit. The heater unit selectively provides heat. The cryogenic gas injection unit selectively injects cold gas. The heater unit is disposed in the separate intake plenum. The cryogenic gas injection unit injects substantially all of the cold gas into the output plenum.

The separate intake and output plenums are spiral plenums each having a central cavity. The central cavities of the separate intake and output plenums are in communication with each other.

Each separate spiral intake and spiral output plenum has an intake and output port respectively. The ports are arranged and configured in a parallel relationship. The plenums are symmetrically disposed with respect to each other.

In a second embodiment the separate spiral intake and spiral output plenums each have an intake and output port respectively, and the intake and output ports are antisymmetrically disposed with respect to each other across a diagonal. The separate intake and output plenums are arranged and configured in an antisymmetrical relationship with respect to each other.

The separate intake and output plenums are separated from each other and the apparatus further comprises an insulating barrier disposed into the separation between the intake and output plenums.

The invention may include a plurality of first units for providing heating and cooling, a junction plenum for communicating input and output of gas to and from the plurality of first units, and a termination unit for providing a predetermined duct termination. The termination unit is coupled to the junction plenum. The junction plenum is coupled to each of the plurality of first units. A quick release mechanism is provided for coupling together the termination unit, junction plenum and the plurality of first units. The quick release mechanism permits assembly and disassembly of the plurality of first unit, junction plenum and termination unit without substantial expenditure of time and effort.

The quick release mechanism is a plurality of quick release lockable fasteners.

The termination unit is a selected one of a plurality of termination assemblies. Each termination assembly is characterized by a distinguishable distribution of intake and output gas flows.

The unit for providing heating/cooling is controlled in response to temperature requirements of the part under test. In particular the first unit for providing heating/cooling is controlled by proportional, integral and derivative control in response to the temperature of the part under test.

The invention is also a method for temperature stress screening a part under test comprising the steps of selectively providing heat in a first plenum, communicating gas from the first plenum to a second plenum, blowing the gas from the second plenum to the part under test, and selectively providing cooling to the gas in the second plenum. The steps of selectively providing heat to the plenum and selectively providing cooling to the second plenum are selectively performed in response to the temperature of the part under test. As a result the thermal screening of the part under test is reliably and accurately controlled.

The method further comprises the step of providing heat to the first plenum and cooling to the second plenum by releasably coupling a heating/cooling unit to the first and second plenums by use of a plurality of quick release lockable fasteners.

The invention can still further be characterized as an improvement in an apparatus for providing thermal stress screening to a part under test. The apparatus comprises the elements of a source of heat, a source of cooling, a blower, and a plenum assembly for intake and output of heated and cooled gas. The gas is heated and cooled by the sources of heating and cooling, drawn into the plenum assembly and output therefrom by the blower. The improvement comprises a plurality of modular units. Each unit includes at least one of the elements of the apparatus. Each modular unit is coupled together by a plurality of quick release lockable fasteners.

The improvement further comprises a plurality of the apparatus for thermal stress screening, and a plenum junction assembly for selectively distributing gas intake and output from the plurality of apparatus. The improvement further comprises a plurality of quick release lockable fasteners for coupling the plenum junction assembly to the plurality of apparatus.

The invention is depicted in the following drawings wherein like elements are referenced by like numerals.

The invention and its various embodiments may now be better understood by turning to the following detailed description.

DETAILED DESCRIPTION OF THE PREFERRED EMBODIMENTS

Thermal cycling of semiconductor components has come to be recognized as an environmental process through which an average of 77% of the flaws of production of hardware may be detected as opposed to an average of 23% detectable through vibrational testing. Thermal cycling to detect production flaws is defined as thermal stress screening and should be performed in such a manner that the temperature of the unit or part under test can be changed at a maximum rate of 22 degrees C. per minute. Typical prior art units do not accomplish this rapid change unless the gas is brought across the part surface at a rate of 25–30 feet per second. Prior art units were often incapable of thermal stress screening by virtue of their inability to create a gasflow across the part at a sufficiently high flow rate. Furthermore, prior art oven art chamber sizes cannot be specifically suited for each profile or size of the virtually unlimited variety of units which are to be tested or which will be placed within the oven or chamber.

What is described below is a variable temperature process and system which accurately and reliably subjects the part under test to the temperature cycle which is programmed into the microprocessor. It can be reliably guaranteed that within the specified error brackets that the part under test will actually be subjected to the programmed temperatures for the periods of time selected and will vary between temperatures at the rates selected.

An environmental chamber for providing thermal stress screening is comprised of a plurality of modular components which may be quickly assembled and disassembled for ease of maintenance and repair. In particular, a heating/cooling unit is coupled by means of a plurality of quick release lockable fasteners to a plenum module. The plenum module in turn is coupled by means of additional quick release lockable fasteners to a blower module. The plenum module in turn is comprised of a heater plenum which communicates with a blower plenum. Gas is drawn into the heater plenum and passed over heating coils which are disposed into the heating plenum from the heating/cooling module. The gas is then communicated to a blower plenum. Cryogenic nitrogen gas is selectively provided to the blower plenum from the heating/cooling module. The selectively heated or cooled gas is then expelled from the blower plenum by means of a blower which extends into the blower plenum from the blower module. Selective heated and cooled gas is directed to a part under test as selectively activated through proportional, integral and derivative control in response to the temperature requirements of the part under test and not in response to the gas delivered to the part or from the blower plenum.

Figure 11:
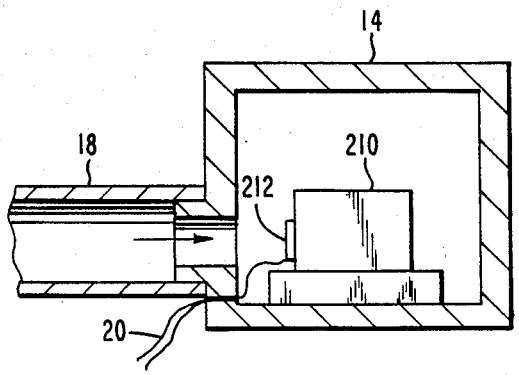
FIG. 11 shows the part under test with the temperature sensor directly mounted thereon, both located within the environmental chamber.

The unit blows dry nitrogen gas across the part under test 210 as shown in FIG. 11 at 30 feet per second. A temperature sensor 212 is mounted directly under the part under test to provide a feedback signal. Heated or cooled nitrogen gas is provided from a source as needed to keep the part under test on the preprogrammed rate of change curve. In the illustrated embodiment the source unit includes a source unit having more than 6,000 watts of electrical heating capacity and approximately 9,000 watts of cooling capacity based upon cryogenic liquid nitrogen gas at −320 degrees F. What results is a thermal stress screening apparatus which is small in size, can vary between low and high temperatures at high rates of change, and has virtually no downtime for repair or maintenance when used in engineering or production test lines.

Figure 1:
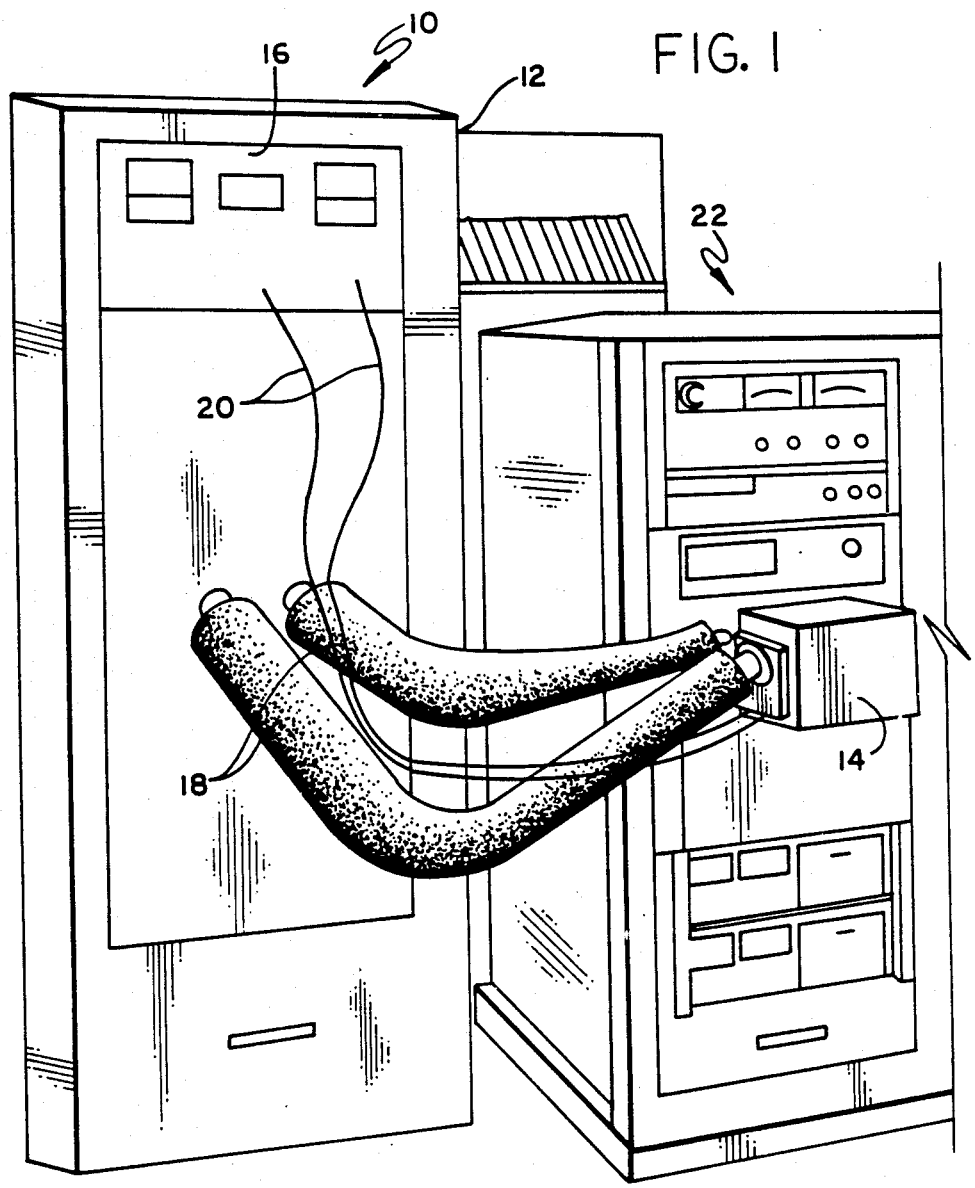
FIG. 1 is a front plan view of an assembled cabinet containing the thermal stress screening apparatus of the invention.
Figure 10:
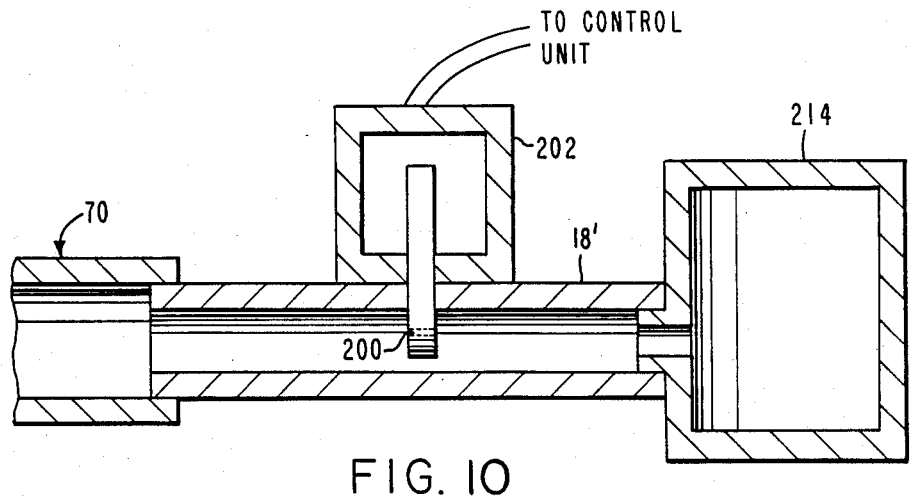
FIG. 10 shows the small hole through the solenoid valve to allow gas to constantly bleed through the valve when the system is operating.

Turn now to FIG. 1 which is a perspective view of the variable temperature process system, generally denoted by reference numeral 10 and shown installed within a cabinet 12, for delivering temperature controlled dry nitrogen to an exposure chamber 14 in which a part is placed for testing. System 10 includes an electronic control unit 16 within the upper portion of cabinet 12. A thermal source unit (not shown in FIG. 1) is contained within the middle portion of cabinet 12 with a conventional power supply unit (also not shown) contained within the lower portion of cabinet 12. The controlled dry nitrogen gas is supplied to the part under test via insulated delivery hoses 18 connected through appropriate plumbing to source 214 as shown in FIG. 10. The unit under test within environmental chamber 14 is coupled to control unit 16 by a thermocouple or other temperature sensing means 212. The thermocouple (as shown in FIG. 11) is directly coupled to the part within environmental chamber 14 and is connected to control unit 16 by means of thermocouple wires 20. The unit under test within environmental chamber 14 is then monitored by conventional test equipment such as generally denoted by reference numeral 22, which test equipment plays no part within the system 10 of the invention and thus will not be further discussed.

Figure 2:
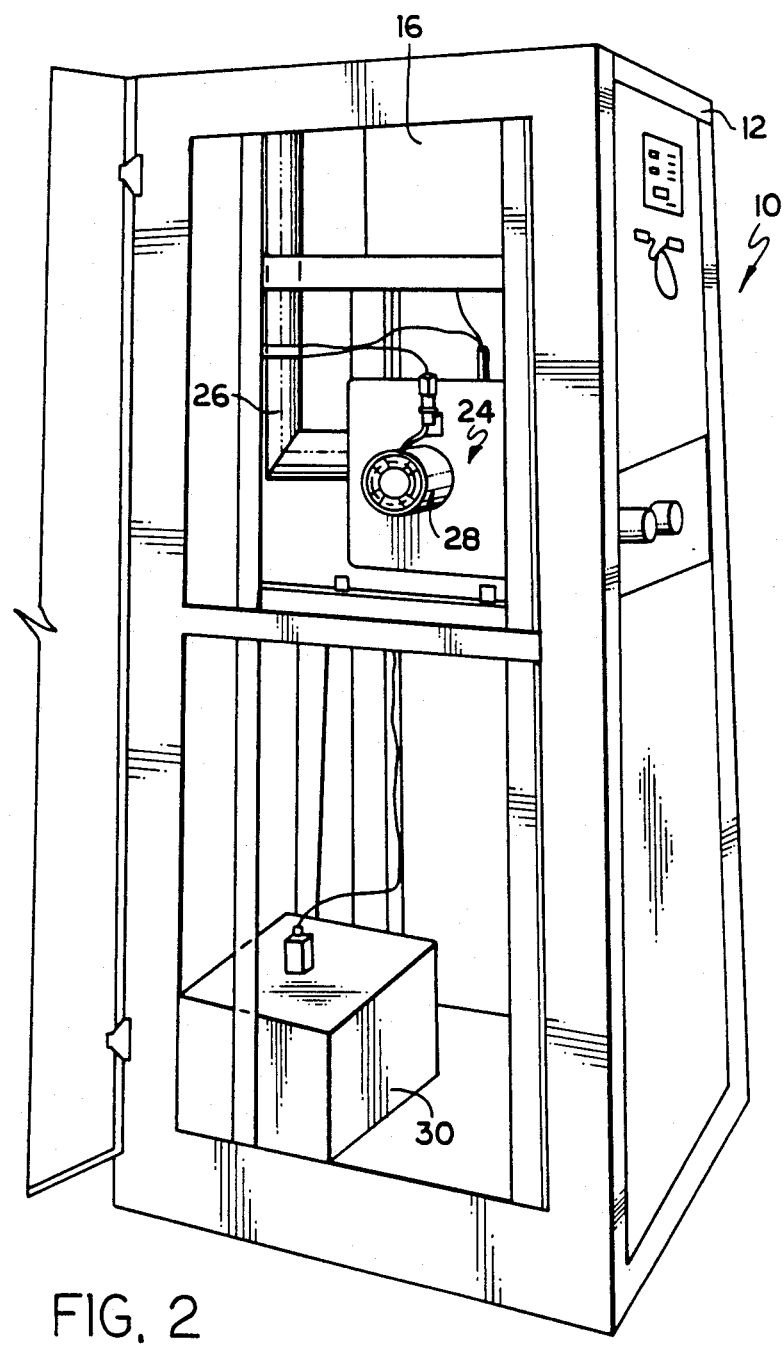
FIG. 2 is a side view of the cabinet of FIG. 1 with the side panel opened showing a single modular thermal unit installed within the cabinet.

Turn to FIG. 2 which illustrates a side perspective view of system 10 with the side of cabinet 12 opened. Cabinet 12 is shown in isolation from the other elements within FIG. 1 and hoses 18 have been removed. Control unit 16 is clearly shown in the upper portion of cabinet 12 and below is thermal source unit 24. Cryogenic dry nitrogen is provided through an insulated delivery conduit 26 to source unit 24. In the illustration of FIG. 2 that side of source unit 24 is illustrated showing motor submodule 28. The lower portion of cabinet 12 shows conventional power supply 30 which provides electrical power to source unit 24 and control unit 16. It can be readily appreciated that cabinet 12 has a substantial amount of additional space wherein additional units like thermal source unit 24 may be accommodated as discussed below.

Figure 3:
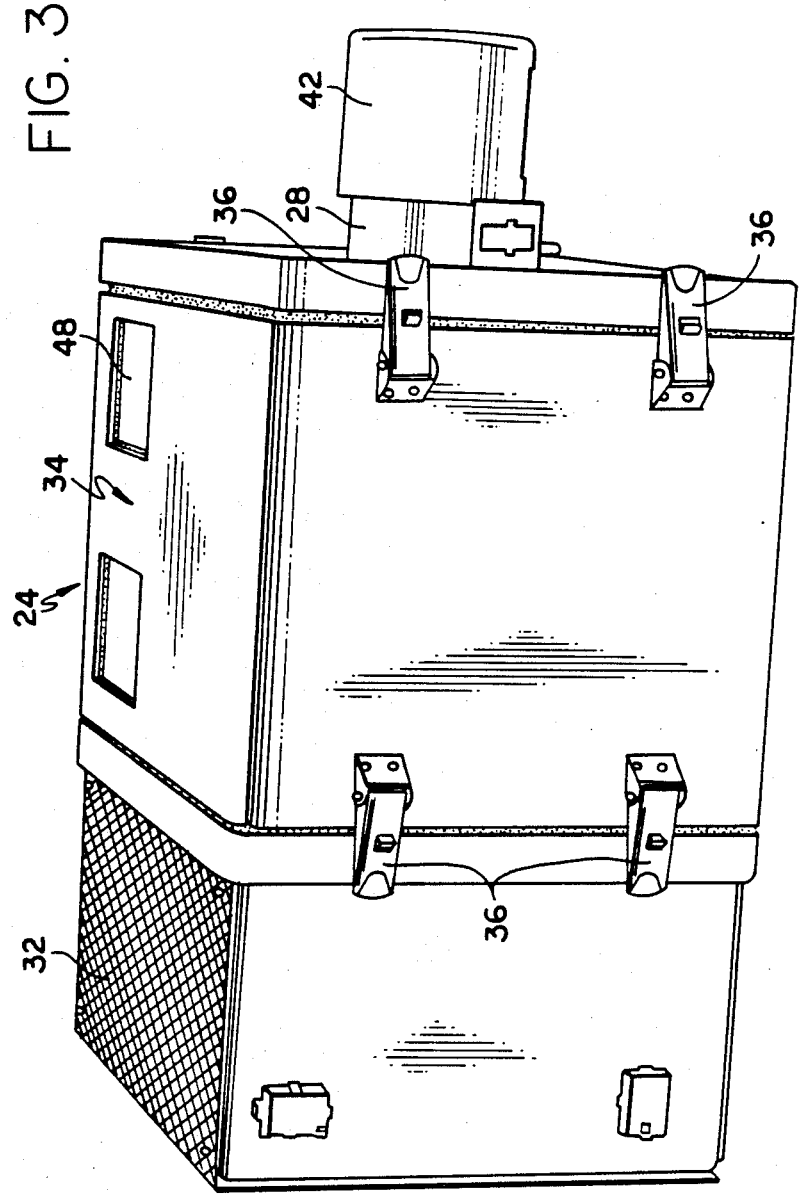
FIG. 3 is a perspective view in enlarged scale of the singular, modular thermal unit shown in FIG. 2.

First consider source unit 24 in greater detail by turning to the perspective view of FIG. 3. FIG. 3 shows a perspective view of a single source unit 24 in enlarged scale and in an assembled configuration. Source unit 24 is comprised of a heater/cooler submodule 32, a central plenum submodule 34 and motor submodule 28. As illustrated in FIG. 3 each of the submodules 28, 32 and 34, are coupled together through quick-connect, lockable latches 36. Two of such latches 36 are shown in FIG. 3 on the right hand side connecting motor submodule 28 to plenum submodule 34. The opposing side of source unit 24 is provided with an additional two latches 36 coupling motor submodule 28 and plenum submodule 34. Similarly, heater/cooler submodule 32 and plenum submodule 34 are coupled by four quick connect latches 36, two of which are shown in FIG. 3.

Figure 4:
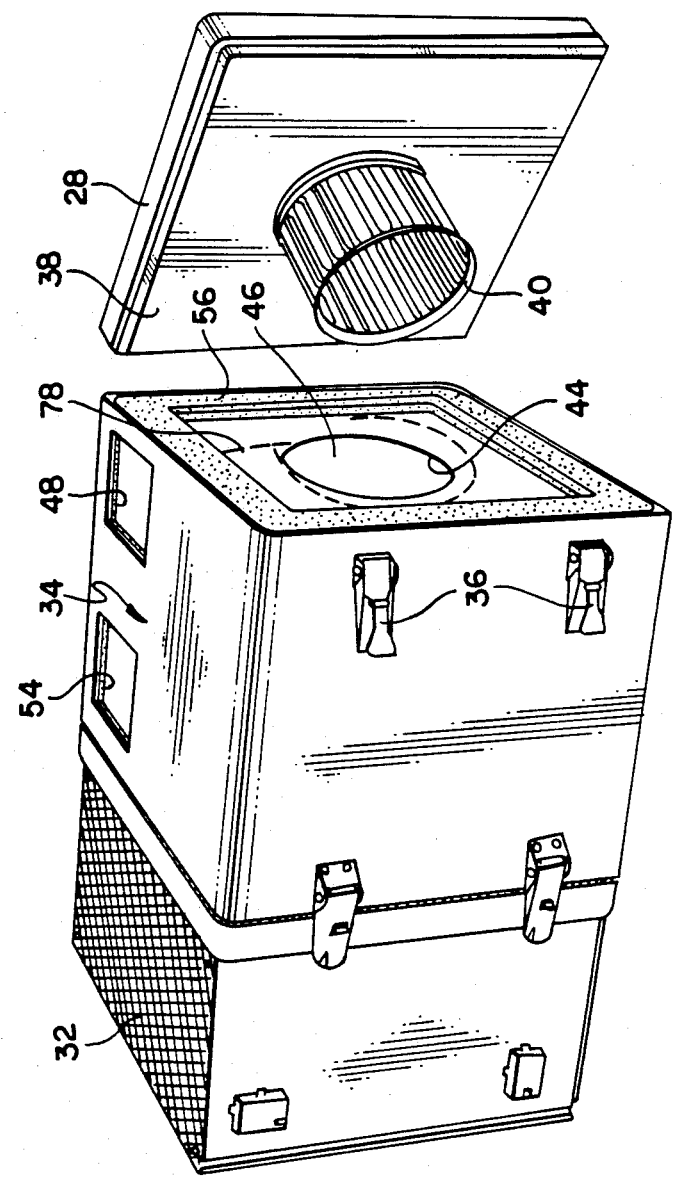
FIG. 4 is a perspective view of the modular unit of FIG. 3 with the fan motor submodule removed and placed to one side.

Turn now to FIG. 4 wherein motor submodule 28 has been disconnected from plenum submodule 34 by release of its corresponding latches 36. The perspective view of FIG. 4 clearly illustrates that motor submodule 28 is comprised of a flat smooth inner plate 38. Centered within plate 38 is a motor of which the squirrel cage impeller 40 is shown in FIG. 4, while motor housing 42 is illustrated in FIG. 3. Impeller 40 is disposed within a receiving cylindrical opening within a blower plenum, generally denoted by reference numeral 46. Outlet 48 of blower plenum 46 is visible in the upper right hand corner of plenum submodule 34 in FIGS. 3 and 4 and will be described in greater detail in connection with FIG. 6. Similarly, included within plenum submodule 34 is a heater plenum 50 (not shown in FIGS. 3 and 4) whose intake port 54 is illustrated in the upper left hand corner of plenum submodule 34 in FIGS. 3 and 4. Motor submodule 28 is coupled in a gastight manner with plenum submodule 34 by means of the sealing action between plate 38 and a perimeter gasket 56 provided along the opposing and mating edge of plenum submodule 34. Sealing of plate 38 against gasket 56 is insured by a compressive force applied between plate 38 and gasket 56 by means of latches 36.

Figure 5:
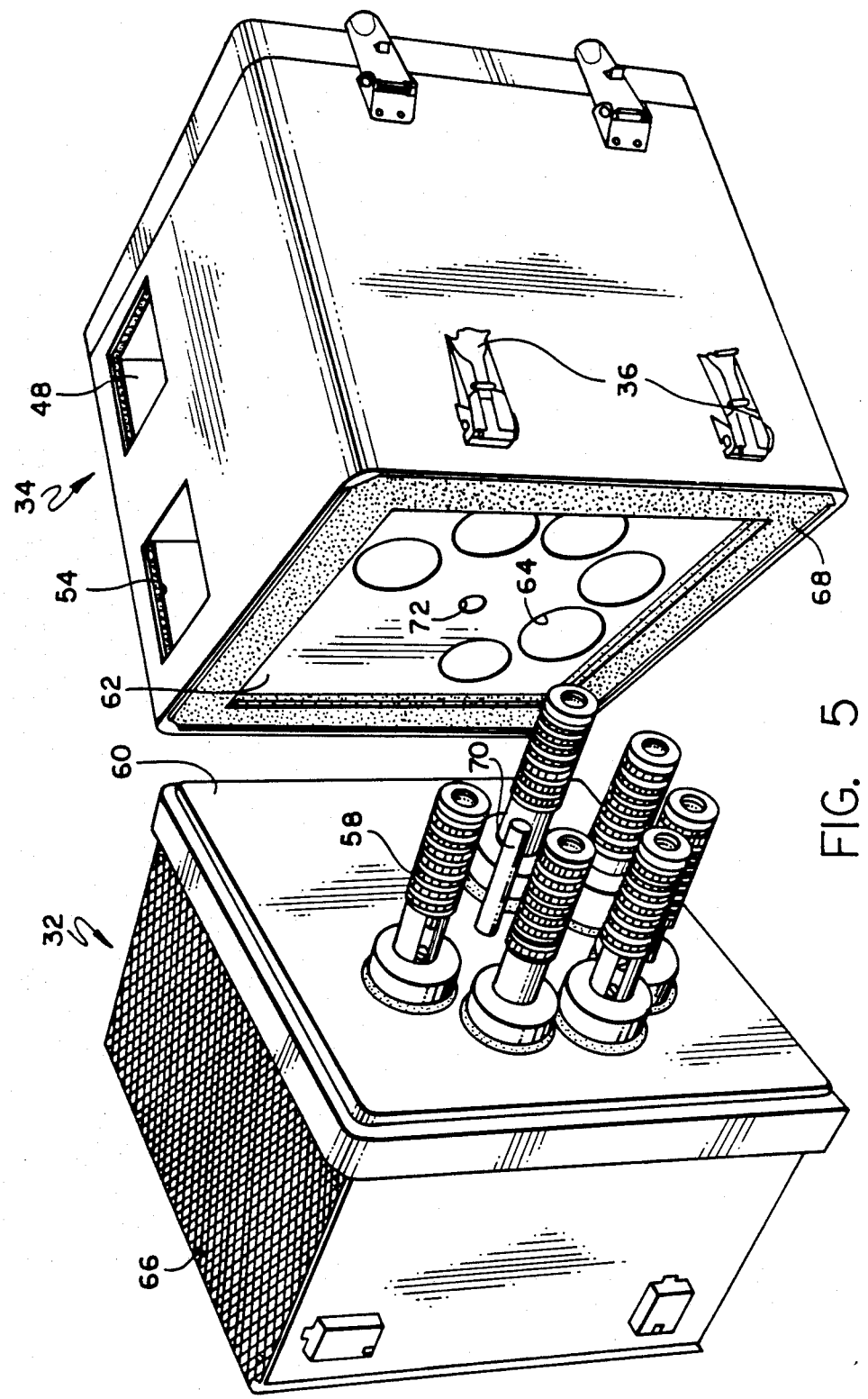
FIG. 5 is a perspective view of the module of FIG. 4 showing an opposing heater submodule removed and placed to the side.

Turn now to FIG. 5 wherein plenum submodule 34 and heater/cooler submodule 2 are shown in perspective view with heater/cooler submodule 32 disconnected from plenum submodule 34. In the illustrated embodiment, six heater coils 58 extend from a facing plate 60 into a heater plenum 52, which is described in greater detail in FIG. 6, and the outer wall 62 of which is shown in FIG. 5. Each heater coil 58 extends through a corresponding circular aperture 64 in exterior wall 62 of heater plenum 52. Heater/cooler submodule 32 contains within its rear cabinet 66 conventional electric components for supplying controlled amounts of electrical power to heater coils 58. As before, plate 60 is compressibly pressed against a perimeter gasket 68 by means of latches 36 to provide a gastight seal between plate 60 of the heater/cooler submodule 32 and plenum submodule 34.

Also extending through the center of plate 60 is a nitrogen delivery tube 70 which has a length approximately equal to the length of each heater coil 58. Nitrogen delivery tube 70 extends through a corresponding mating aperture 72 in outer wall 62 of heater plenum 52. Aperture 72 is defined within the center of heater plenum 52 so that the liquid nitrogen is directed to the very center of plenum submodule 34 as will be better described and discussed in connection with FIG. 6. Dry liquid nitrogen is delivered through delivery tube 70 through appropriate conventional insulated tubing and coupling extending through cabinet 66 of heater/cooler submodule 32. A conventional cryogenic coupling (not shown) is provided on the exterior of cabinet 66 whereby a conventional liquid nitrogen, pressurized dewar tank may be coupled to heater/cooler submodule 32. A cryogenic valve included within submodule 32 is serially aligned with delivery tube 70 between the liquid nitrogen supply tank and delivery tube 70. Thus, controlled amounts and durations of liquid nitrogen may be supplied through tube 70. The liquid nitrogen is at least partially vaporized within tube 70, and in any case flashes into gaseous form upon exiting delivery tube 70. It has been determined that the nitrogen control valve must be provided with a thickened valve face since the number of openings and closings of the valve is substantially greater than what would be encountered during normal cycling of the valve.

A small hole 200 of approximately 0.015 inch in diameter is drilled through the solenoid valve 202 which opens and closes the (45 psi) liquid nitrogen line 18'. This small hole constantly bleeds gaseous nitrogen to the blower plenum while the system is turned "on". This keeps dry nitrogen gas in positive pressure within the system so that no moisture from the ambient seeps into the recirculating dry nitrogen gas system.

It may be readily appreciated by examining FIGS. 3-5 collectively that the various elements of source unit 24 can be quickly assembled and disassembled for maintenance with very little effort or time. Each submodule 32 or 28 may be decoupled from plenum submodule 34 in a few seconds. Heater elements 58 can be replaced simply by removing or unscrewing the units from their sockets. Similarly, impeller 40 or motor 42 may similarly be accessed in a few seconds and quickly replaced with a standardized spare submodule 28.

Figure 6:
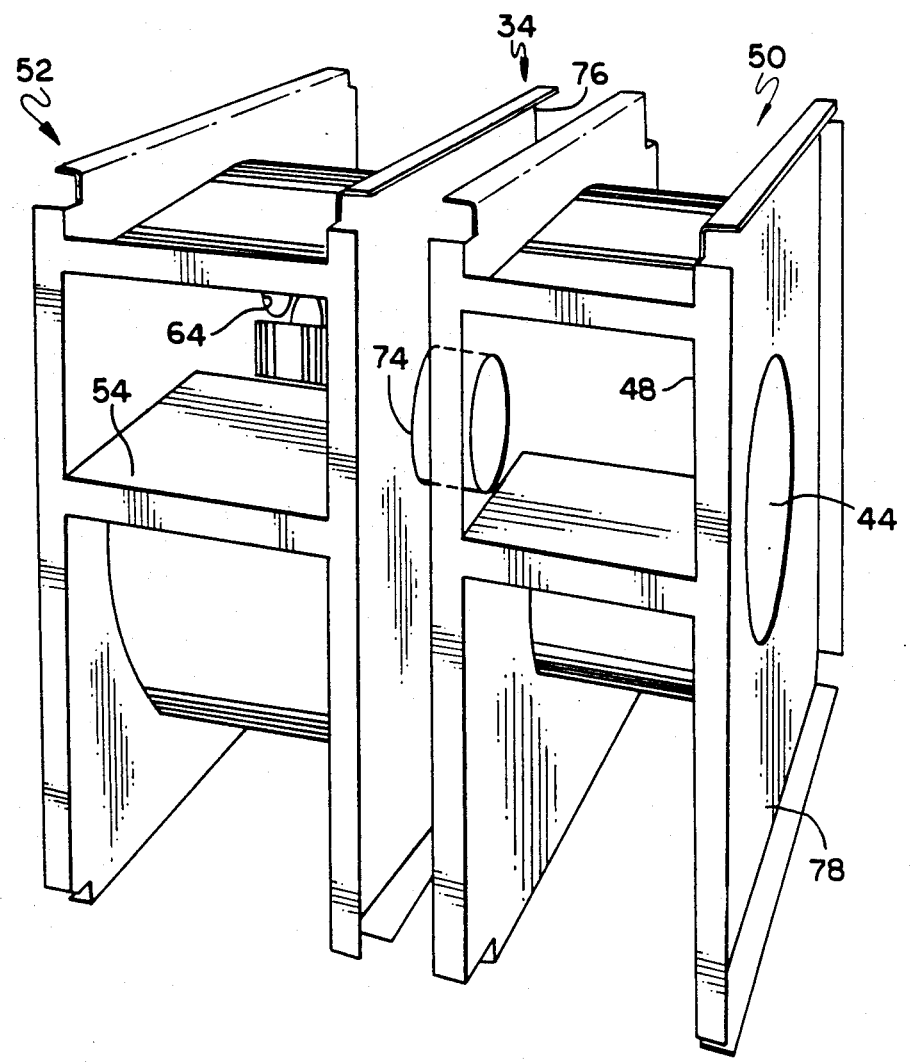
FIG. 6 is a perspective view of the plenum assembly contained within the module of FIGS. 3–5 as shown in isolation disassembled from the module.

Turn now to the perspective depiction of FIG. 6 wherein heater plenum 52 and blower plenum 50 have been removed from plenum module 34 and shown in isolation. Plenums 50 and 52 have been rotated 90 degrees from the orientation which the plenums assume in FIGS. 3-5 so that intake port 54 and output port 48 are facing the viewer of FIG. 6. Each plenum 50 and 52 is spirally shaped, having a central cylindrical cavity 44 and spiralling outward in a counterclockwise direction as viewed from the right in FIG. 6 toward corresponding port 54 or 48 as appropriate. Central cavity 44 of blower plenum 50 is entirely open to allow the insertion of impeller 40 within cavity 44. Central cavity 44 of plenum 52 is open to the exterior through outer plate 62 through opening 72 through which nitrogen delivery tube 70 extends. However, each individual cavity 44 of heater plenum 52 and blower plenum 50 directly communicate with each other in the center of plenum module 54 through a short cylindrical extension 74 as shown in dotted outline in FIG. 6. Plenums 50 and 52 are separated from each other by means of a cylindrical extension 74 to provide a space 76 for insulation between plenums 50 and 52. Space 76 separating plenums 50 and 52 is filled with a conventional −100 degree C. to 500 degree C. insulation (not shown).

Figure 7:
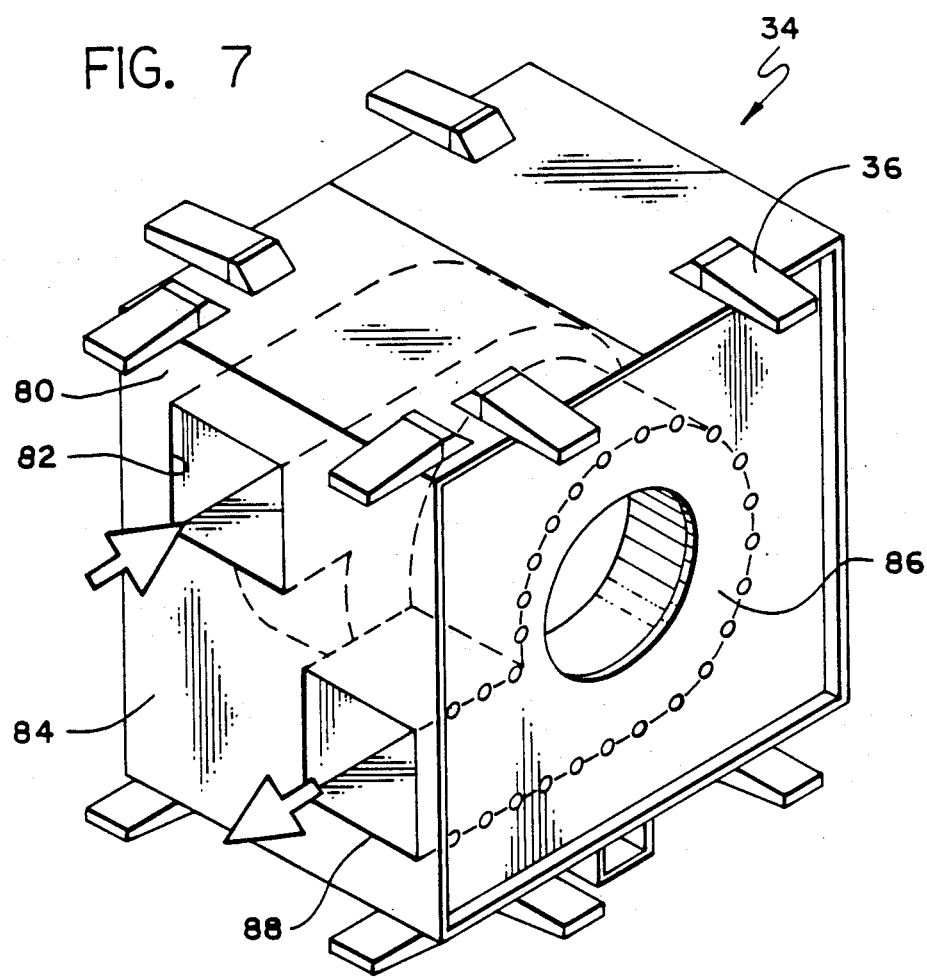
FIG. 7 is a diagrammatic perspective view of a second embodiment of the central element of a module showing reversed gas plenums within the central element.

The spiral shape of plenums 50 and 52 can be seen by dotted outline 78 as best depicted in FIG. 7, and is also partially seen in FIG. 6.

Consider now the manner in which the submodules of FIGS. 3-5 coact with each other within plenums 50 and 52 as shown in FIG. 6 to provide the heating and cooling of the invention. Impeller 40 draws gas from the center of cavity 44 of plenum 50 and impels the gas radially outward along helical plenum 50 toward output port 48. Gas is drawn into the center of cavity 44 of blower plenum 50 through cylindrical extension 74. Cylindrical extension 74 in turn communicates with central axial cavity 44 of heater plenum 52. The end of nitrogen delivery tube 70 terminates at or near the opening of cylindrical extension 74 so that the dry nitrogen flashing into gas essentially fills and floods central cavity 44 of blower plenum 50. Impeller 40 thus serves not so much to pump nitrogen from plenum 52 but to evacuate the nitrogen gas from cavity 44. In fact, at some rates of release, the expanding nitrogen gas may serve to assist in driving impeller 40 rather than acting as a drag upon the impeller. The pressure of expansion of the nitrogen delivered to cavity 44 of plenum 50 may in fact be so great that some means for relief of excess pressure is required. In one embodiment a small bleed hole may be provided through exterior wall 46 of plenum 50 or otherwise provided in the output circuit, such as within output ducting or hoses.

When heater coils 58 are activated and nitrogen is turned off, impeller 40 tends to create a partial pressure within cavity 44 of plenum 50, thereby drawing gas through extension 74 from center cavity 44 of heater plenum 52. Gas is thus drawn into cavity 44 of heater plenum 52 through its spiral plenum from intake port 54 across heater coils 58. Each heater coil has an output of approximately 1,000 watts or more. Collectively, then, heater coils 58 are able to deliver 6,000 watts of thermal heat to the gas circulated through submodule 34. Thus it can now be appreciated that the separation 76 between plenums 50 and 52 assists in providing a quicker thermal response when thermal operation is switched from heating to cooling. Plenums 50 and 52, being comprised of metal, have a heat capacity and thus serve to contribute to the thermal inertia of system 10. After heated gas is drawn through plenum 52 for a period of time, and it is desired to provide cooling gas, the heaters are deactivated and liquid nitrogen delivered through tube 70. The nitrogen gas (at −320 degrees F.) is essentially delivered to blower plenum 50 first and not to the heated surfaces of heater plenum 52. Thus, only the thermal inertia contributed by plenum 50 immediately figures into cooling operation. In other words, the delivered nitrogen is heated only to the extent of the residual heating capacity within plenum 50 before delivery to the part under test. The warmed nitrogen is then returned from the part under test through a return hose 18 to plenum 52 where it serves to cool plenum 52 before being recirculated. However, the nitrogen gas, which is initially delivered to the part under test, is not subjected to the warming effects of the residual heat within plenum 52.

Turn now to FIG. 7 wherein a second embodiment of the invention is illustrated in a diagrammatic perspective view. FIG. 7 shows a plenum submodule 34 with the remaining submodules removed. Substantially identical plenums to heater plenum 52 and blower plenum 50 as shown in FIGS. 2-6 are employed, with the exception that plenum orientation has been reversed. That is, heater plenum 80 has an intake port 82 which appears in the upper left corner of face 84 of submodule 34. Blower plenum 86 is reversed so that its output port 88 appears in the lower right corner of ace 84 of submodule 34. Thus intake port 82 and output port 88 appear on a diagonal face 84 in an adjacent relationship such as depicted in FIGS. 2-6. Otherwise, the embodiment of FIG. 7 is substantially identical to that shown in FIGS. 2-6. The embodiment of FIG. 7 further differs in that the separation or insulation between plenums 80 and 86 has been omitted.

Figure 8:
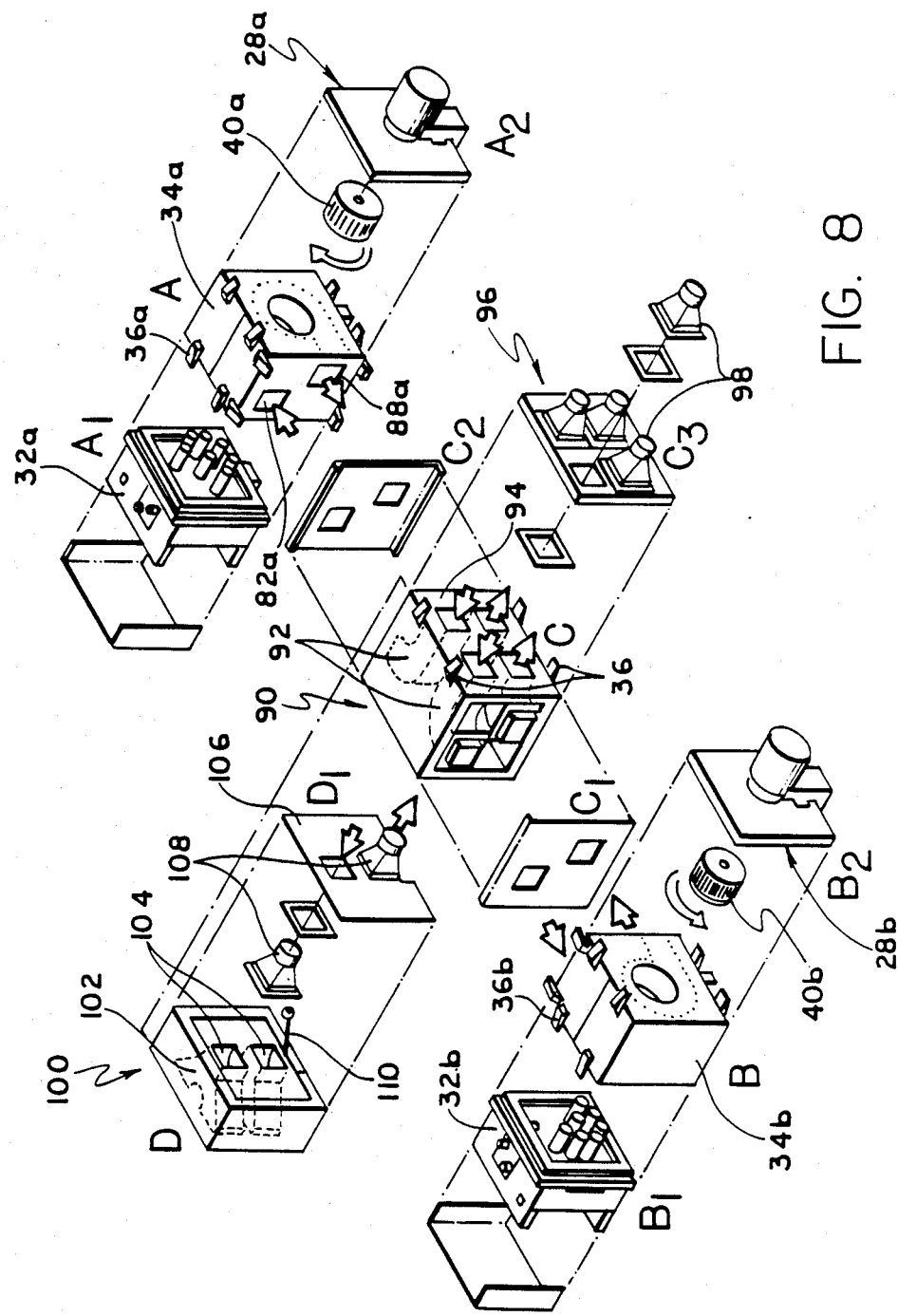
FIG. 8 is a diagrammatic perspective view of a pair of modules as shown in FIG. 7 shown in exploded view and combinable in a plurality of options.

Turn now to the diagrammatic perspective, exploded view of FIG. 8 wherein two plenum submodules 34 are modularly coupled to provide a dual unit. In FIG. 8 a first plenum submodule 34a is combined with a second plenum submodule 34b. Each submodule has a corresponding heater submodule 32a and 32b, respectively, which is identical to heater/cooler submodule 32 described in connection with FIGS. 1-6. Similarly, corresponding motor submodules 28a and 28b are also provided. Impellers 40a and 40b are shown in exploded view apart from the main portion of their corresponding modules 28a and 28b. Impeller 40a is driven in a clockwise direction as depicted in FIG. 8 while impeller 40b is driven in a counterclockwise direction. As before, modules 28a, 32a and 34a on the one hand, and modules 28b, 32b and 34b on the other hand, are each coupled together through quick connect latches 36a or 36b, respectively. Submodules 34a and 34b are similarly connected to a junction plenum assembly, generally denoted by the reference numeral 90. Junction plenum assembly 90 includes four curved ducts arranged and configured within assembly 90 to appropriately couple with intake and output ports of said modules 34a and 34b. In other words, ducts 92 are arranged on the diagonal on the opposing faces of junction assembly 90 facing submodules 34a and 34b. The direction of gas flow is indicated in FIGS. 7 and 8 by diagrammatic arrows. Ports 82a, 82b and 88a, 88b (only 82a and 88a of which are visible in FIG. 8) are thus communicated by means of ducts 92 to a single face 94 of junction assembly 90. Terminations of the upper two ducts 92 are coupled to the intake ports 82a and 82b of submodules 34a and 34b, while the lower two ports are coupled to the output ports 88a and 88b of submodule 34a and 34b, respectively.

Various terminations may then be coupled through latches 36 on junction plenum assembly 90 for on-site delivery. For example, one option is the use of a four-ducted termination, generally denoted by reference numeral 96. Termination 96 is comprised of a frame in which four duct adaptors 98 are disposed. Each duct adaptor communicates with the corresponding port on face 94 of junction plenum assembly 90 to adapt the square shaped plenum to a round output suitable for hose coupling.

Alternatively, termination 96 may be replaced by a switching plenum generally denoted by reference numeral 100. Switching plenum 100 includes two Y-shaped junction plenums 102 which will join both output or intake ports together in a single duct. Two duct ports 104 are then provided and may be terminated by termination 106 which include transition terminations 108 adapting the square shaped ducts 104 to circular hose fittings. As before, both terminations 96 and 100 are quickly connected to assembly 90 by means of latches 36. The system thus may be quickly configured between one configuration and the other by clamping on the appropriate termination unit.

Termination unit 100 further includes a lever 110 which operates a flapper valve (not shown) which will selectively close the left or right side of ducts 102 so that either unit 34b or 34a may be alternatively selected by operation of lever 110. Therefore, submodule 34a may be operated solely as a heating unit while submodule 34b may be operated solely as a cooling unit. The delivery of cooled or warmed gas to the part under test is then mechanically switched through operation of lever 110 in a quick manner virtually independent of any thermal inertia in the system so that thermal shocks or very sudden changes in temperature may then be applied to the part under test.

Figure 9:
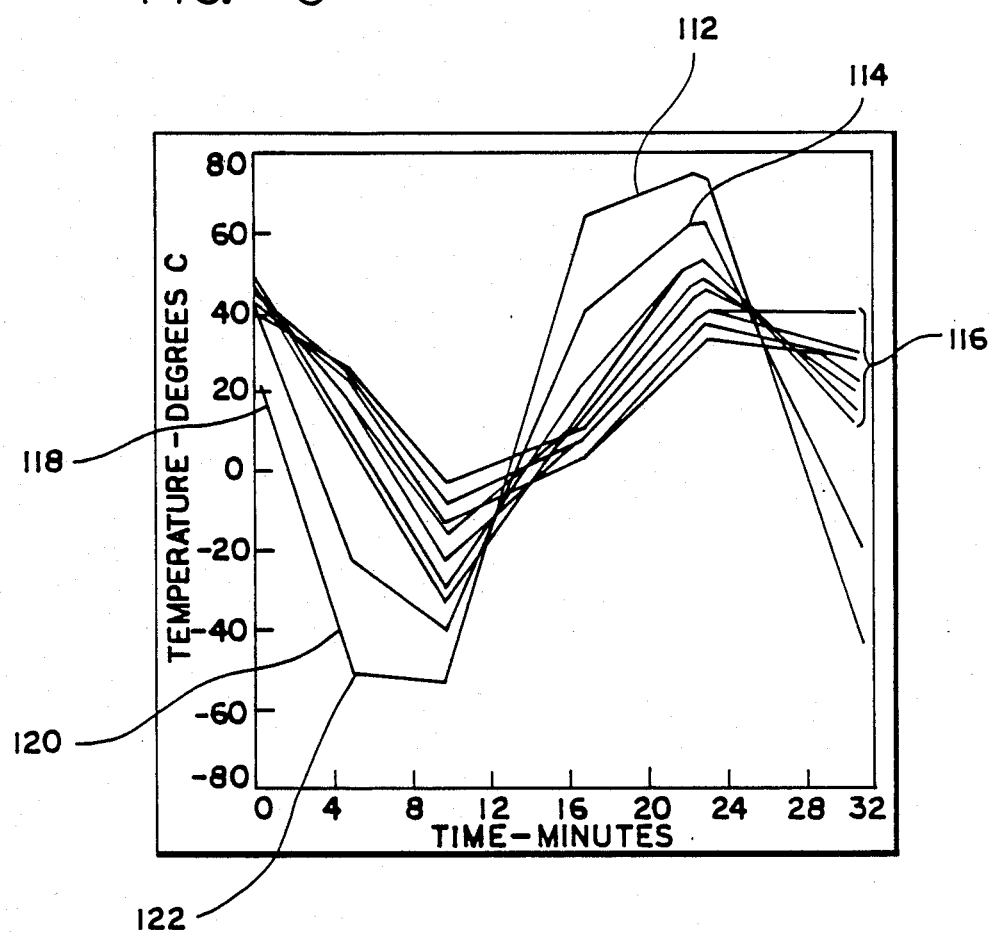
FIG. 9 is a graph of temperature against time illustrating the difference in performance between an environmental chamber of the present invention as compared to prior art chambers.

Turn to FIG. 9 wherein the performance of system 10 as illustrated in FIGS. 1-8 is graphically depicted. The vertical axis is temperature in degrees C. while the horizontal axis represents time in minutes. Curve 112 represents a typical temperature cycle as measured within the supply chamber of a typical prior art environmental chamber. The temperature chamber begins at 20 degrees C. and is then cooled over four minutes to approximately −50 degrees C. It is held between −50 and −55 degrees C. for approximately four to five minutes and thereafter rapidly heated in approximately six to seven minutes time to approximately 65 degrees C. and thereafter held for five to six minutes between 65 degrees C. and 75 degrees C. Finally, the chamber temperature is then rapidly dropped from approximately 75 degrees C. to −40 degrees C. in six to eight minutes. Curve 114 represents the temperature of the gas actually delivered to the part under test. By comparison of curves 112 and 114 it can be readily appreciated that the temperature of the gas delivered to the part under test lags the temperature and time of the gas in the source chamber. Curves 116 represent a family of curves for parts under test as measured during repeated experiments utilizing the temperature cycling represented by curves 112 and 114. Comparison of curves 116 with curves 112 and 114 further illustrates the lag in temperature and time between the part under test and the temperature of the cycling gas either at the origin represented by curve 112 or its destination, represented by curve 114. The graph of FIG. 9 dramatically illustrates that not only is there a temperature and time lag between the actual temperature of the part under test, represented by curves 116, but the repeatability of the temperature cycling for any given part during a repetition of the temperature cycling is extremely poor.

Under the present invention, the temperature which is monitored is the temperature of the part under test. Heating and cooling is applied through a temperature feedback as measured in a programmable controller. Cool nitrogen or heated recirculated gas is supplied according to programmed control in response to the measured feedback. Therefore, if curve 112 represented the preprogrammed temperature control, the part would be maintained at the temperatures and times of curve 112 within predetermined error limits by the application of whatever heating or cooling operation was required. The temperature of gas delivered to the part is then largely immaterial as long as it is adequate to hold the part to the cycling indicated by curve 112. The control which is used in the invention is a proportional, integral and derivative (PID) control. Thus, although heating and cooling is provided on a full-on or full-off basis, the number of repetitions and length of hot or cold injection is determined by an integrated look-ahead proportioning according to conventional PID control. For example, a number of sustained nitrogen bursts may e injected into the system at point 118 on curve 112. However, as point 120 is approached the number and/or duration of cold nitrogen injections is increased in anticipation of the leveling of the temperature cycle which has been preprogrammed to begin at point 122 on curve 112. As a result, the actual measured temperature of the part under test can be maintained within ½ to 2 degrees C. of the preprogrammed temperature represented by curve 112, according to arbitrarily selected error limitations. Repeated temperature cyclings of the part under test will thus follow the preprogrammed curve 112 within the boundaries of the selected error envelope. Variations as depicted by the family of curves 116 in FIG. 9 will not occur in a system devised according to the invention.

Many modifications and alterations may be made by those having ordinary skill in the art without departing from the spirit and scope of the invention. Thus the illustrated embodiment has been set forth only for the purpose of example and should not be taken as limiting the invention which is defined in the following claims.

What is claimed is:

1. Apparatus for conducting thermal stress screening of a part being tested, comprising:
    a chamber;
    a temperature sensor located in said chamber;
    an electronic control unit electrically coupled to said temperature sensor;
    first means for providing an intake plenum and an output plenum in communication with one another;
    second means for blowing gas whereby gas is moved from said intake plenum to said output plenum, said second means being coupled to said first means;
    third means for providing heat to said intake plenum;
    fourth means for providing cool dry gas to said output plenum;
    a first passageway coupling said output plenum to said chamber and a second passageway coupling said chamber to said input plenum;
    said electronic control unit being electrically coupled to said third means for controlling the amount of heat provided to said intake plenum (and eventually to said chamber); and also electrically coupled to said fourth means for controlling the amount of cool dry gas provided to said output plenum; and
    wherein said fourth means further comprises a source of liquified gas coupled to a delivery tube for delivering cool dry gas to said output plenum, and a cryogenic valve having an input port coupled to said source of liquified gas and its output port coupled to said delivery tube for controlling the flow of cool dry gas from said source to said delivery tube; said cryogenic valve having a small hole therethrough so as to permit a constant controlled flow of cool dry gas therethrough even when said valve is in its closed position, whereby a positive pressure is maintained in said plenum and in said chamber.

2. The apparatus according to claim 1 where said electronic control unit is electrically coupled to said cryogenic valve.

3. The apparatus according to claim 2 wherein said small hole has a diameter substantially equal to 0.015 inches.

4. The apparatus of claim 2 further including a part under test located in said chamber, said temperature sensor being directly coupled to said part whereby said electronic control unit controls said third means and said fourth means as determined by sensing the temperature of said part under test.

5. The apparatus of claim 4 wherein said electronic control unit monitors the temperature of said part under test and controls said third means nd said fourth means to produce a desired temperature change rate of the part under test.

* * * * *